(12) United States Patent
Collette

(10) Patent No.: US 7,517,907 B2
(45) Date of Patent: Apr. 14, 2009

(54) PHARMACEUTICAL/COSMETIC COMPOSITIONS COMPRISING A NOVEL RARBETA RECEPTOR-ACTIVATING LIGAND

(75) Inventor: Pascal Collette, Le Cannet (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/409,085

(22) Filed: Apr. 24, 2006

(65) Prior Publication Data

US 2007/0004698 A1    Jan. 4, 2007

Related U.S. Application Data

(63) Continuation of application No. PCT/FR2004/002718, filed on Oct. 22, 2004.

(30) Foreign Application Priority Data

Oct. 23, 2003   (FR) .................................. 03 12410

(51) Int. Cl.
    C07D 317/00   (2006.01)
    A61K 31/335   (2006.01)
(52) U.S. Cl. ....................................... 514/463; 549/453
(58) Field of Classification Search ............... 514/184, 514/463; 549/206, 453
    See application file for complete search history.

(56) References Cited

OTHER PUBLICATIONS

Charpentier et al., "Synthesis, Structure—Affinity Relationships, and Biological Activities of Ligands Binding to Retinoic Acid Receptor Subtypes", J. Med. Chem., 1995, pp. 4993-5006, No. 38, No. 26, 1995 American Chemical Society.

*Primary Examiner*—Taylor Victor Oh
(74) *Attorney, Agent, or Firm*—Buchanan, Ingersoll & Rooney P.C.

(57) ABSTRACT

Novel ligand compounds having the structural formula (I):

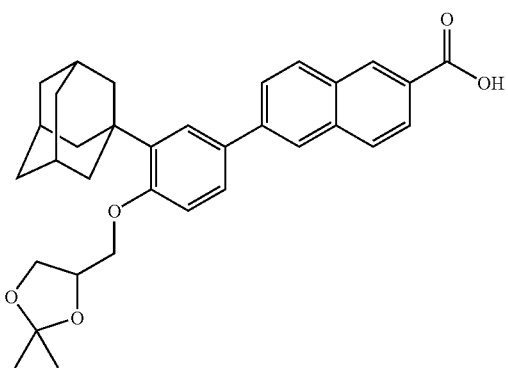

and the salts and optical/geometrical isomers thereof are suited for formulation into pharmaceutical compositions useful in human or veterinary medicine, or, alternatively, into cosmetic compositions.

11 Claims, 1 Drawing Sheet

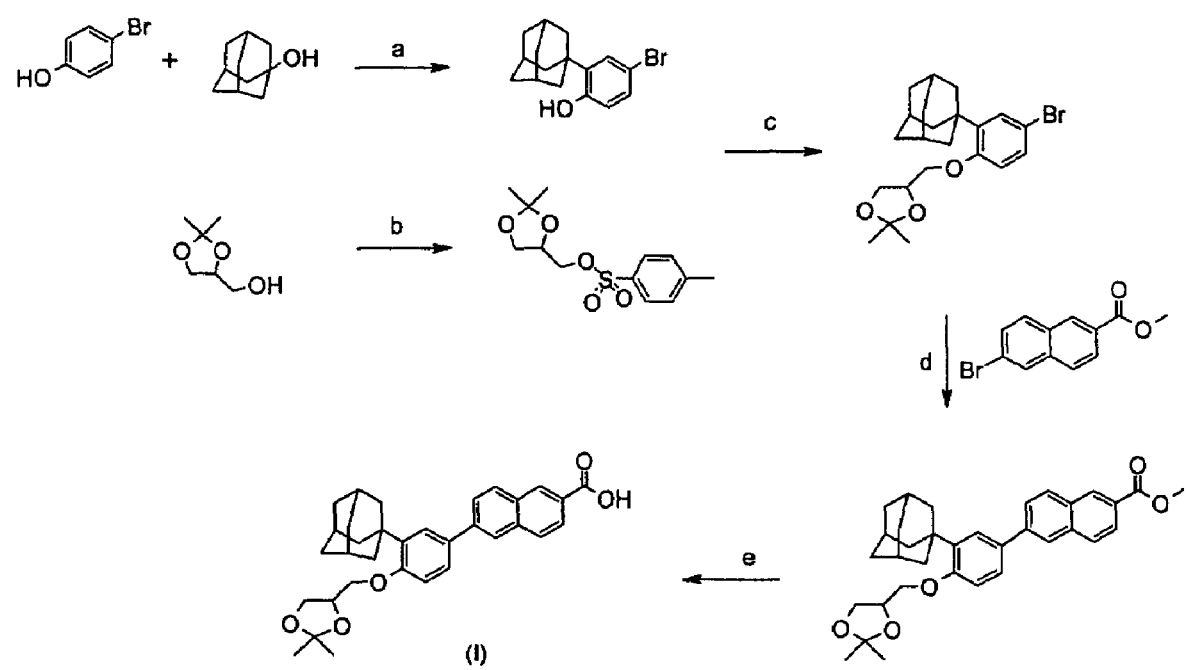

PHARMACEUTICAL/COSMETIC COMPOSITIONS COMPRISING A NOVEL RARBETA RECEPTOR-ACTIVATING LIGAND

CROSS-REFERENCE TO PRIORITY/PCT APPLICATIONS

This application claims priority under 35 U.S.C. § 119 of FR 03/12410, filed Oct. 23, 2003, and is a continuation of PCT/FR 2004/002718, filed Oct. 22, 2004 and designating the United States (published in the French language on May 6, as WO 2005/040148 A1; the title and abstract were also published in English), each hereby expressly incorporated by reference and each assigned to the assignee hereof.

BACKGROUND OF THE INVENTION

1. Technical Field of the Invention

The present invention relates to a novel compound, which is an RARbeta receptor-activating ligand, as a novel and useful industrial bioactive agent. This invention also relates to a process for preparing same and to pharmaceutical compositions containing the subject novel compound suited for administration in human or veterinary medicine, or alternatively in cosmetic compositions.

2. Description of Background and/or Related and/or Prior Art

Compounds with activity of retinoid type (vitamin A and its derivatives) are widely described in the literature as having activity in cell proliferation and differentiation processes. These properties provide this class of compounds great potential in the treatment or prevention of numerous pathologies, and more particularly in dermatology and in the modulating nuclear retinoic acid receptors (RARs).

RAR receptors activate transcription by binding to DNA sequence elements, known as RAR response elements (RAREs), in the form of a heterodimer with retinoid X receptors (known as RXRs).

Three subtypes of human RARs have been identified and described: RARα, RARβ and RARγ.

The prior art sets forth a large number of chemical compounds having activating activity on receptors of RAR type. Particularly exemplary are the aromatic bicyclic compounds described in EP-0-722,928, aromatic heterocyclic compounds described in EP-0-732,328, heterocyclic biaryl compounds described in WO 97/29100, biaromatic propynyl compounds described in WO 97/33856, and aromatic heterocyclic biaryl compounds described in EP-0-816,352.

SUMMARY OF THE INVENTION

A novel compound has now been developed which, surprisingly, has the particularity of being a ligand that is a specific activator of retinoic acid receptors subtype beta.

Thus, the present invention features a compound having the following structural formula (I):

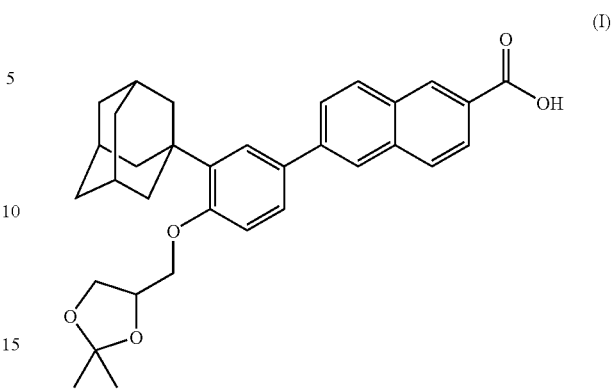

and the salts of the compound of formula (I) and also the optical and geometric isomers of said compound of formula (I).

When the compound according to the invention is in the form of a salt, it is preferably an alkali metal or alkaline earth metal salt, or else a zinc salt or a salt of an organic amine.

The present invention also features the process for preparing the compound of formula (I), in particular according to the reaction scheme shown in the attached FIGURE of Drawing:

a) 2-adamantyl-4-bromophenol can be obtained by electrophilic substitution of adamantanol on the 4-bromophenol in the presence of sulfuric acid, $H_2SO_4$;

b) the primary alcohol of 1,2-isopropylidene glycerol is activated, for example, by introduction of a tosyl group, such as tosyl chloride TsCl, in the presence of pyridine;

c) then, the compound obtained is substituted on the phenol group of the 2-adamantyl-4-bromophenol described above, for example in the presence of potassium carbonate $K_2CO_3$ and of dimethylformamide DMF;

d) this bromide is then coupled with methyl 6-bromo-2-napthoate, for example under Negishi-type coupling conditions (with (i) Mg, tetrahydrofuran THF, (ii) $ZnCl_2$, (iii) Ar—Br, $NiCl_2$, diphosphinopropane ethylene Dppe), so as to obtain methyl 6-[3-adamantan-1-yl-4-(2,2-dimethyl[1,3]dioxolan-4-ylmethoxy)phenyl]naphthalene-2-carboxylate;

e) finally, a saponification, for example in the presence of sodium hydroxide NaOH, makes it possible to obtain 6-[3-adamantan-1-yl-4-(2,2-dimethyl[1,3]dioxolan-4-ylmethoxy)phenyl]naphthalene-2-carboxylic acid.

The compounds according to the invention have activating properties on RARbeta-type receptors. This RARbeta receptor-activating activity can in particular be measured in a transactivation assay by means of the dissocation constant Kdapp (apparent), the AC50 (concentration giving 50% of the activity of the reference molecule) and also by means of the % activation.

According to the invention, the expression "activator of RARbeta-type receptors" means any compound which, for the RARbeta subtype, has a dissociation constant Kdapp of less than or equal to 1 µM, and an AC50≦100 nM, in the transactivation assay as described in Example 2.

The compound according to the invention is a specific RARβ receptor type activator, i.e., it has a ratio R of RARβ Kdapp to RARα or RARγ Kdapp of less than or equal to $10^{-1}$. Preferably, R is less than or equal to 0.05, and more advantageously less than or equal to 0.02.

The present invention also features the compound of formula (I) as described above, as a medicinal active agent.

The compound according to the invention is particularly suitable in the following fields of treatment:

- for treating dermatological complaints, conditions or afflictions associated with a keratinization disorder relating to cell differentiation and proliferation, in particular for treating common acne, comedonal acne, polymorphic acne, acne rosacea, nodulocystic acne, acne conglobata, senile acne, and secondary acne such as solar acne, medication-related acne or occupational acne;
- for treating other types of keratinization disorders, in particular ichthyosis, ichthyosiform conditions, Darier's disease, palmoplantar keratoderma, leukoplakia and leukoplakiform conditions, and cutaneous or mucosal (buccal) lichen;
- for treating other dermatological complaints, conditions or afflictions with an inflammatory immunoallergic component, with or without cell proliferation disorder, and in particular all forms of psoriasis, whether cutaneous, mucosal or ungual, and even psoriatic rheumatism, or cutaneous atopy, such as eczema, or respiratory atopy, or alternatively gingival hypertrophy;
- for treating all dermal or epidermal proliferations, whether benign or malignant, and whether of viral or nonviral origin, such as common warts, flat warts and verruciform epidermodysplasia, oral or florid papillomatoses, T lymphoma, and proliferations that may be induced by ultraviolet radiation, in particular in the case of basal cell and spinocellular epithelioma, and also any cutaneous precancerous lesion such as keratoacanthomas;
- for treating other dermatological disorders such as immune dermatoses, such as lupus erythematosus, immune bullous diseases and collagen diseases, such as scleroderma;
- in the treatment of dermatological or general complaints, conditions or afflictions with an immunological component;
- for treating certain ophthalmological disorders, in particular corneopathies;
- for preventing or curing the stigmata of epidermal and/or dermal atrophy induced by local or systemic corticosteroids, or any other form of cutaneous atrophy;
- in the treatment of any cutaneous or general complaint, condition or affliction of viral origin;
- in the treatment of skin disorders caused by exposure to UV radiation, and also for repairing or combating aging of the skin, whether photoinduced or chronological aging, or for reducing pigmentations and actinic keratosis, or any pathology associated with chronological or actinic aging, such as xerosis;
- for combating sebaceous function disorders, such as the hyperseborrhoea of acne or simple seborrhoea;
- for preventing or treating cicatrization disorders, or for preventing or repairing stretch marks, or else for promoting cicatrization;
- in the treatment of pigmentation disorders, such as hyperpigmentation, melasma, hypopigmentation or vitiligo;
- in the treatment of lipid metabolism complaints, conditions or afflictions such as obesity, hyperlipidemia, or non-insulin-dependent diabetes;
- in the treatment of inflammatory complaints, conditions or afflictions such as arthritis;
- in the treatment or prevention of cancerous or precancerous conditions;
- in the prevention or treatment of alopecia of various origins, in particular alopecia caused by chemotherapy or radiation;
- in the treatment of disorders of the immune system, such as asthma, type I sugar diabetes, multiple sclerosis, or other selective dysfunctions of the immune system; and
- in the treatment of complaints, conditions or afflictions of the cardiovascular system, such as arteriosclerosis or hypertension.

The present invention also features pharmaceutical compositions comprising, in a physiologically acceptable medium, at least one compound of formula (I) as defined above.

The present invention also features novel medicinal compositions suited especially for treating the abovementioned complaints, conditions or afflictions which comprise, formulated into a pharmaceutically acceptable support that is compatible with the mode of administration selected for this composition, the compound of formula (I), an optical isomer thereof or a salt thereof.

The compositions according to the invention may be administered (regime or regimen) orally, enterally, parenterally, topically or ocularly. The pharmaceutical composition is preferably packaged in a form that is suitable for topical application.

Via the oral route, the composition may be in the form of tablets, gel capsules, sugar-coated tablets, syrups, suspensions, solution, powders, granules, emulsions, suspensions of microspheres or nanospheres or lipid or polymer vesicles allowing controlled release. Via the parenteral route, the composition may be in the form of solutions or suspensions for infusion or for injection.

The compound according to the invention is generally administered at a daily dose of approximately 0.01 mg/kg to 100 mg/kg of body weight, in 1 to 3 dosage intakes.

The compound is administered systemically at a concentration generally of from 0.001% to 10% by weight, preferably from 0.01% to 1% by weight, relative to the weight of the composition.

Via the topical route, the pharmaceutical compositions according to the invention are more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or of lipid or polymer vesicles or gels or polymer patches allowing controlled release.

The compound is administered topically at a concentration generally of from 0.001% to 10% by weight, preferably from 0.01% to 1% by weight, relative to the total weight of the composition.

The compound of formula (I) according to the invention also finds an application in the cosmetics field, in particular in body and hair hygiene, and especially for treating acne-prone skin, for promoting hair regrowth or for limiting hair loss, for combating the greasy appearance of the skin or the hair, in protection against the harmful effects of sunlight or in the treatment of physiologically dry skin, and for preventing and/or combating photoinduced or chronological aging.

This invention thus also features cosmetic compositions comprising, formulated into a physiologically acceptable support, the compound of formula (I).

The expression "a physiologically acceptable medium" means a medium that is compatible with the skin and, optionally, with its integuments (eyelashes, nails, hair) and/or the mucous membranes.

The present invention also features the non-therapeutic administration of a cosmetic composition comprising the compound of formula (I) for preventing and/or treating the signs of aging and/or dry skin.

This invention also features the non-therapeutic administration of a cosmetic composition comprising the compound of formula (I) for body or hair hygiene.

The cosmetic compositions according to the invention containing, in a cosmetically acceptable support, the compound of formula (I) or an optical or geometric isomer thereof or a salt thereof, may in particular be in the form of a cream, a milk, a gel, suspensions of microspheres or nanospheres or lipid or polymer vesicles, impregnated pads, solutions, sprays, mousses, sticks, soaps, washing bases or shampoos.

The concentration of compound of formula (I) in the cosmetic composition is preferably from 0.001% to 3% by weight, relative to the total weight of the composition.

The pharmaceutical and cosmetic compositions as described above may also contain inert additives, or even pharmacodynamically active additives as regards the pharmaceutical compositions, or combinations of these additives, and in particular:
  wetting agents;
  flavor enhancers;
  preservatives such as para-hydroxybenzoic acid esters;
  stabilizers;
  moisture regulators;
  pH regulators;
  osmotic pressure modifiers;
  emulsifiers;
  UV-A and UV-B screening agents;
  antioxidants;
  emollients;
  moisturizers;
  anti-seborrheic or anti-acne agents;
  antibiotics;
  anti-fungal agents;
  agents for promoting hair regrowth;
  nonsteroidal anti-inflammatory agents;
  carotenoids, and in particular β-carotene;
  anti-psoriatic agents;
  eicosa-5,8,11,14-tetraynoic acid and eicosa-5,8,11-triynoic acid, and esters and amides thereof;
  retinoids, i.e., natural or synthetic RXR receptor ligands;
  corticosteroids or oestrogens;
  α-hydroxy acids and α-keto acids or derivatives thereof;
  ion-channel blockers such as potassium-channel blockers;
  or alternatively, more particularly for pharmaceutical compositions, in combination with medicinal products known to interfere with the immune system (for example, cyclosporin, FK 506, glucocorticoids, monoclonal antibodies, cytokines, or growth factors, etc.).

Of course, one skilled in this art will take care to select the optional compound(s) to be added to these compositions in such a way that the advantageous properties intrinsically attached to the present invention are not, or are not substantially, adversely affected by the envisaged addition.

The present invention also features a cosmetic regime or regimen for rendering the skin more attractive, wherein a cosmetic composition as defined above is applied to the skin.

An example of obtaining the active compound of formula (I) according to the invention, biological activity results thereof and also various specific formulations based on the compound will now be given, it being understood that same are intended only as illustrative and in nowise limitative. In said examples to follow, all parts and percentages are given by weight, unless otherwise indicated.

The FIGURE of Drawing represents the reaction scheme for a method for preparing the compound of formula (I).

EXAMPLE 1

Synthesis of 6-[3-adamantan-1-yl-4-(2,2-dimethyl[1,3]dioxoian-4-ylmethoxy)phenyl]naphthalene-2-carboxylic acid 1. Preparation of 2,2-Dimethyl[1,3]dioxolan-4-ylmethyl toluene-4-sulfonate 57.2 g (300 mmol) of tosyl chloride are added to a solution of 39.6 g (300 mmol) of (2,2-dimethyl[1,3]dioxolan-4-yl) methanol in 170 ml of pyridine at 0° C. The mixture is stirred overnight, diluted with ether, washed with a 1N hydrochloric acid solution until the aqueous phase is at acid pH, and then washed with a saturated sodium hydrogen carbonate solution.

The organic phase is then dried over sodium sulfate, filtered and evaporated. A colorless oil is obtained (m=79.3 g, yield=92%).

2. Preparation of 2-Adamantan-1-yl-4-bromophenol 51.9 g (300 mmol) of 4-bromophenol and 45.7 g (300 mmol) of adamantan-1-ol are dissolved in 150 ml of dichloromethane; 15 ml of 98% sulfuric acid are slowly run in and the reaction medium is stirred at ambient temperature for two days. The medium is evaporated to dryness, taken up with water, neutralized to pH=7-8, filtered, taken up in THF, dried over $MgSO_4$, evaporated, and purified on a silica column, elution being carried out with a 10/90 ether/heptane mixture. A thick oil is obtained (m=58 g, yield=63%).

3. Preparation of 4-(2-Adamantan-1-yl-4-bromophenoxymethyl)-2,2-dimethyl[1,3]dioxolane 10 g (32.5 mmol) of 2-adamantan-1-yl-4-bromophenol and 4.95 g (35.8 mmol) of potassium carbonate are mixed in 140 ml of DMF.

A solution of 2,2-dimethyl[1,3]dioxolan-4-ylmethyl toluene-4-sulfonate (11.2 g, 39 mmol) in 60 ml of DMF is run dropwise into the reaction medium while heating the latter to 100° C. The reaction medium is stirred at 100° C. for 24 h. The reaction medium is poured onto ice-cold water and extracted with ether. The organic phase is washed with water and then with brine, dried over $MgSO_4$, filtered and evaporated. The 14 g of crude product obtained are purified on a column of fine silica (6-35 μm), elution being carried out with a 50/50 dichloromethane/heptane mixture.

After evaporation of the fractions, 7.51 g (55%) of a yellow powder are obtained (melting point mp: 91° C.).

4. Preparation of Methyl 6-[3-Adamantan-1-yl-4-(2,2-dimethyl[1,3]dioxolan-4-ylmethoxy)phenyl]naphthalene-2-carboxylate 962 mg (39.6 mmol) of magnesium granules are wetted with a minimum of THF. A solution of 7.4 g (17.6 mmol) of 4-(2-adamantan-1-yl-4-bromophenoxymethyl)-2,2-dimethyl[1,3]dioxolane, 50 ml of THF and 300 μl (3.5 mmol) of dibromoethane is run dropwise into the suspension of magnesium. The reaction medium is heated at the reflux of the THF for 1 h 30 min and then brought back to 20° C. 5.1 g (37.6 mmol) of zinc chloride, dried and melted under vacuum beforehand, are added while keeping the temperature of the medium at 20° C., and then 50 ml of THF are added and the medium is stirred at 20° C. for 1 h 30 min. 10 g (37.6 mmol) of methyl 6-bromonaphthalene-2-carboxylate are added in small fractions while maintaining the temperature of the medium at 20° C., and then 300 mg of NiCl$_2$/dppe complex and 50 ml of THF are added and the reaction medium is stirred at ambient temperature for 15 h. The reaction medium is then treated with a saturated ammonium chloride solution and extracted with ether. The organic phase is filtered, washed with water, and then dried and concentrated under reduced pressure. The residue obtained is then purified by chromatography on a silica column (elution being carried out with 70 heptane/30 dichloromethane).

A white solid is obtained (m=8.3 g, yield=89%, mp=117° C.).

5. Synthesis of 6-[3-Adamantan-1-yl-4-(2,2-dimethyl[1,3]dioxolan4-ylmethoxy)phenyl]naphthalene-2-carboxylic acid 2 g (50 mmol) of sodium hydroxide and 25 ml of methanol (i.e., 25 ml of a 2N solution of methanolic sodium hydroxide) are added to 1 g (1.9 mmol) of methyl 6-[3-adamantan-1-yl-4-(2,2-dimethyl[1,3]dioxolan-4-ylmethoxy)phenyl]naphthalene-2-carboxylate. The reaction medium is heated at the reflux of methanol for 6 h and then at ambient temperature for 2 days and, finally, evaporated to dryness. The solid residue is taken up in water, and the aqueous phase is acidified to pH=2-3 and extracted with ether. The organic phase is washed with water and then with brine, dried over magnesium sulfate, filtered, and evaporated until only approximately 10 ml of a suspension of the product in ether remains. The crystals are then filtered off and dried. After drying, 862 mg (88%) of a yellowish powder are obtained (mp=287° C.). $^1$H NMR (CDCl$_3$+drop DMSO-d6) (250 MHz): 1.43 (s, 3H), 1.49 (s, 3H), 1.80 (s, 6H), 2.12 (broad s, 3H), 2.18 (s, 6H), 4.05 (m, 2H), 4.16-4.30 (m, 2H), 4.60 (m, 1H), 7.0 (d, J=8.5 Hz, 1H), 7.55 (d, J=8.5 Hz, 1H), 7.6 (s, 1H), 7.78 (d, J=8.5 Hz, 1H), 7.89-8.00 (m, 3H), 8.09 (d, J=10.0 Hz, 1H), 8.63 (s, 1H).

EXAMPLE 2

Transactivation Assay

The activation of receptors with an agonist (activator) in HeLa cells leads to the expression of a reporter gene, luciferase, which, in the presence of a substrate, generates light. The activation of the receptors can thus be measured by quantifying the luminescence produced after incubating the cells in the presence of a reference antagonist. Activating products will displace the antagonist from its site, thus allowing activation of the receptor. The activity is measured by quantifying the increase in light produced. This measurement makes it possible to determine the activating activity of the compound according to the invention.

In this study, a constant is determined which represents the affinity of the molecule for the receptor. Since this value can fluctuate depending on the basal activity and the expression of the receptor, it is referred to as the Kd apparent (Kdapp).

To determine this constant, "crossed curves" of the test product against a reference antagonist, otherwise referred to as reference ligand, 4-(5,5-dimethyl-8-p-tolyl-5,6-dihydronaphthalen-2-ylethynyl)benzoic acid, are realized in 96-well plates. The test product is used at 10 concentrations and the reference antagonist at 7 concentrations. In each, the cells are in contact with a concentration of the test product and with a concentration of the reference antagonist, 4-(5,5-dimethyl-8-p-tolyl-5,6-dihydronaphthalen-2-ylethynyl)benzoic acid.

Measurements are also taken for the total agonist control, otherwise referred to as 100% control (4-[2-(5,5,8,8-tetramethyl-5,6,7,8-tetrahydronaphthalen-2-yl)propenyl]benzoic acid), and the inverse agonist control, otherwise referred to as 0% control, 4-{(E)-3-[4-(4-tert-butylphenyl)-5,5,8,8-tetramethyl-5,6,7,8-tetrahydronaphthalen-2-yl]-3-oxopropenyl}benzoic acid.

These crossed curves make it possible to determine the AC50 values (concentration at which 50% activation is observed) for the reference ligand at various concentrations of test product. These AC50 values are used to calculate the Schild regression by plotting a straight line corresponding to the Schild equation ("quantitation in receptor pharmacology" Terry P. Kenakin, *Receptors and Channels*, 2001, 7, 371-385).

In the case of an agonist, an AC50 value (concentration giving 50% activity) is calculated by plotting the curve of the product at the concentration of the reference ligand that gives 80% activation. The % activation which corresponds to the maximum level of activity obtained is also measured.

The HeLa cell lines used are stable transfectants containing the plasmids ERE-βGlob-Luc-SV-Neo (reporter gene) and RAR (α,β,γ) ER-DBD-puro. These cells are seeded in 96-well plates at a rate of 10,000 cells per well in 100 μl of DMEM medium without phenol red, supplemented with 10% of defatted calf serum. The plates are then incubated at 37° C. and 7% CO$_2$ for 4 hours.

The various dilutions of the test product, of the reference ligand (4-(5,5-dimethyl-8-p-tolyl-5,6-dihydronaphthalen-2-ylethynyl)benzoic acid), of the 100% control (4-[2-(5,5,8,8-tetramethyl-5,6,7,8-tetrahydronaphthalen-2-yl)propenyl] benzoic acid, 100 nM) and of the 0% control (4-{(E)-3-[4-(4-tert-butylphenyl)-5,5,8,8-tetramethyl-5,6,7,8-tetrahydronaphthalen-2-yl]-3-oxopropenyl}benzoic acid, 500 nM) are added in a proportion of 5 μl per well. The plates are then incubated for 18 hours at 37° C. and 7% CO$_2$.

The culture medium is removed by turning the plates over, and 100 μl of a 1:1 PBS/luciferin mixture are added to each well. After 5 minutes, the plates are read using a luminescence reader.

|  | RARalpha | | | RARbeta | | | RARgamma | | |
|---|---|---|---|---|---|---|---|---|---|
|  | Kdapp (nM) | AC50 (nM) | % activation | Kdapp (nM) | AC50 (nM) | % activation | Kdapp (nM) | AC50 (nM) | % activation |
| Ex. 1 | 8000 | 1800 | 20 | 60 | 12 | 100 | 4000 | 2000 | 40 |

The results obtained with the compound according to the invention clearly show that the subject compound has great specificity for the RARbeta receptor subtype compared with the other two subtypes RARalpha and RARgamma (ratio of the Kdapp values R=0.015), this clearly demonstrating an increase in the signal, and in the luminescence in the presence of the reference antagonist. The compound according to the invention is therefore clearly a selective activator of RARbeta receptors.

EXAMPLE 3

Formulation Examples

In this example, various specific formulations based on the compound according to the invention have been illustrated.

A - ORAL ROUTE:

(a) 0.2 g Tablet:
| | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral suspension in 5 ml ampoules:
| | |
|---|---|
| Compound of Example 1 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g Tablet:
| | |
|---|---|
| Compound of Example 1 | 0.500 g |
| Pregelatinized starch | 0.100 g |
| Microcrystalline cellulose | 0.115 g |
| Lactose | 0.075 g |
| Magnesium stearate | 0.010 g |

(d) Oral suspension in 10 ml ampoules:
| | |
|---|---|
| Compound of Example 1 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B - PARENTERAL ROUTE:

(a) Composition:
| | |
|---|---|
| Compound of Example 1 | 0.002 g |
| Ethyl oleate | qs 10 g |

(b) Composition:
| | |
|---|---|
| Compound of Example 1 | 0.05% |
| Polyethylene glycol | 20% |
| 0.9% NaCl solution | qs 100 |

(c) Composition:
| | |
|---|---|
| Compound of Example 1 | 2.5% |
| Polyethylene glycol 400 | 20% |
| 0.9% NaCl solution | qs 100 |

(d) Injectable cyclodextrin composition:
| | |
|---|---|
| Compound of Example 1 | 0.1 mg |
| β-cyclodextrin | 0.10 g |
| Water for injection | qs 10.00 g |

C - TOPICAL ROUTE:

(a) Ointment:
| | |
|---|---|
| Compound of Example 1 | 0.020 g |
| Isopropyl myristate | 81.700 g |
| Liquid petroleum jelly fluid | 9.100 g |
| Silica ("Aerosil 200" marketed by Degussa) | 9.180 g |

(b) Ointment:
| | |
|---|---|
| Compound of Example 1 | 0.300 g |
| White petroleum jelly codex | qs 100 g |

(c) Nonionic water-in-oil cream:
| | |
|---|---|
| Compound of Example 1 | 0.100 g |
| Mixture of emulsifying lanolin alcohols, waxes and oils ("anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:
| | |
|---|---|
| Compound of Example 1 | 0.100 g |
| Polyethylene glycol (PEG 400) | 69.900 g |
| 95% ethanol | 30.000 g |

(f) Nonionic oil-in-water cream:
| | |
|---|---|
| Compound of Example 1 | 1.000 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 9 |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

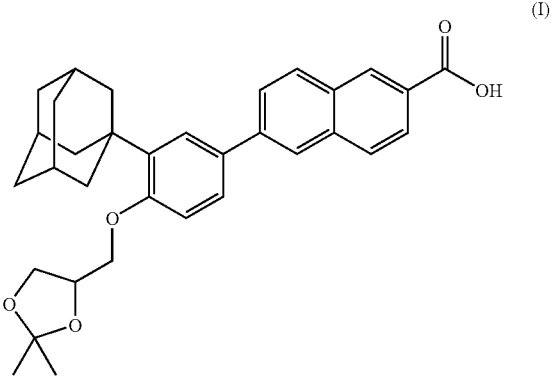

or a salt or isomer thereof.

2. An alkali or alkaline earth metal, or zinc or organic amine salt of a compound as defined by claim 1.

3. A regime or regimen for the treatment of:
common acne, comedonal acne, polymorphic acne, acne rosacea, nodulocystic acne, acne conglobata, senile acne, solar acne, medication-related acne or occupational acne;
ichthyosis, ichthyosiform conditions, Darier's disease, palmoplantar keratoderma, leukoplakia or leukoplakiform conditions, or cutaneous or mucous (buccal) lichen;
cutaneous psoriasis, muscosal psoriasis, ungual psoriasis, psoriatic rheumatism, cutaneous atopy, eczema, respiratory atopy or gingival hypertrophy;
common warts, flat warts, verruciform epidermodysplasia, or oral or florid papillomatoses;
basal cell or spinocellular epithelioma;
keratoacanthomas;
immune dermatoses;
immune bullous diseases;
collagen diseases;
dermatological complaints, conditions or afflictions having an immunological component;
ophthalmological disorders;
stigmata of epidermal and/or dermal atrophy induced by local or systemic corticosteroids, or any other form of cutaneous atrophy;
skin complaints, conditions or afflictions of viral origin;
skin disorders caused by exposure to UV radiation, photoinduced or chronological aging of the skin, or actinic pigmentations and keratoses;
xerosis;
disorders of sebaceous function;
cicatrization disorders or stretch marks; or
pigmentation disorders;
comprising administering to a mammalian organism in need of such treatment, a thus effective amount of a compound as defined by claim 1.

4. A pharmaceutical composition comprising a pharmaceutically effective amount of at least one compound (I) as defined by claim 1, formulated into a physiologically acceptable support therefor.

5. The pharmaceutical composition as defined by claim 4, comprising from 0.001% to 10% by weight of said at least one compound (I).

6. The pharmaceutical composition as defined by claim 4, comprising from 0.01% to 1% by weight of said at least one compound (I).

7. A cosmetic composition comprising a cosmetically effective amount of at least one compound (I) as defined by claim 1, formulated into a physiologically acceptable support therefor.

8. The cosmetic composition as defined by claim 7, comprising from 0.001% to 3% by weight of said at least one compound (I).

9. A regime or regimen for treating the signs of aging and/or dry skin, comprising administering to an individual in need of such treatment, a thus effective amount of at least one compound (I) as defined by claim 1.

10. A regime or regimen for body hair hygiene, comprising administering to an individual in need of such treatment, a thus effective amount of at least one compound (I) as defined by claim 1.

11. A regime or regimen for enhancing the appearance of the skin, comprising topically applying onto the skin of an individual in need of such treatment, a thus effective amount of at least one compound (I) as defined by claim 1.

* * * * *